(12) United States Patent
Ishihara et al.

(10) Patent No.: US 7,785,372 B2
(45) Date of Patent: Aug. 31, 2010

(54) ARTIFICIAL JOINT MEMBER WITH GRAFTED POLYMER SURFACE

(75) Inventors: Kazuhiko Ishihara, 8-17, Iguchi 5-chome, Mitaka-shi, Tokyo (JP) 181-0011; Toru Moro, 1-22-902, Honkomagome 1, Bunkyo-ku, Tokyo (JP) 113-0021; Kozo Nakamura, 23-13, kita-machi 2, Nerima-ku, Tokyo (JP) 179-0081; Yoshio Takatori, 26-16-703, Hakusan 2-chome, Bunkyo-ku, Tokyo (JP) 112-0001; Hiroshi Kawaguchi, 1-16-909, Sendagi 4, Bunkyo-ku, Tokyo (JP) 113-0022; Tomohiro Konno, Tokyo (JP); Tomiharu Matsushita, Hyogo (JP); Shuji Kusumoto, Hyogo (JP)

(73) Assignees: Kabushiki Kaisha Kobe Seiko Sho, Kobe-shi (JP), part interest; Kazuhiko Ishihara, Mitaka-shi (JP), part interest; Kozo Nakamura, Tokyo (JP), part interest; Yoshio Takatori, Tokyo (JP), part interest; Hiroshi Kawaguchi, Tokyo (JP), part interest; Toru Moro, Tokyo (JP), part interest ( * ) Notice: Subject to any disclaimer, the term of this patent is extended or adjusted under 35 U.S.C. 154(b) by 884 days.

(21) Appl. No.: 10/489,112

(22) PCT Filed: Feb. 19, 2003

(86) PCT No.: PCT/JP03/01750

§ 371 (c)(1),
(2), (4) Date: Mar. 10, 2004

(87) PCT Pub. No.: WO03/070289

PCT Pub. Date: Aug. 28, 2003

(65) Prior Publication Data

US 2004/0243249 A1   Dec. 2, 2004

(30) Foreign Application Priority Data

Feb. 19, 2002   (JP)   ............... 2002-042272

(51) Int. Cl.
*A61F 2/30*   (2006.01)
(52) U.S. Cl. ............ 623/23.59; 522/115; 623/23.58
(58) Field of Classification Search ............ 623/23.39, 623/23.58, 22.15, 23.59; 424/423; 522/85, 522/115
See application file for complete search history.

(56) References Cited

U.S. PATENT DOCUMENTS 4,961,954 A * 10/1990 Goldberg et al. ............... 600/36

(Continued)

FOREIGN PATENT DOCUMENTS

EP   722973   7/1996

(Continued)

OTHER PUBLICATIONS

Derwent-Acc-No: 1994-245413 on JP-06178930A patent to Kuroda et al.*

(Continued)

*Primary Examiner*—Paul Prebilic
(74) *Attorney, Agent, or Firm*—Oblon, Spivak, McClelland, Maier & Neustadt, L.L.P.

(57) ABSTRACT

An artificial joint member made of a polymeric material including a portion made of a polymeric substance has a sliding surface composed of a polymer having phosphoryl choline groups. With such an arrangement, the artificial joint member is provided with a sliding part capable of keeping a satisfactory lubricating state for a long time.

8 Claims, 4 Drawing Sheets

U.S. PATENT DOCUMENTS

| | | | |
|---|---|---|---|
| 5,451,428 A | * | 9/1995 | Rupp .................. 427/2.12 |
| 6,005,160 A | * | 12/1999 | Hsiue et al. ............. 427/2.24 |
| 6,228,900 B1 | | 5/2001 | Shen et al. |
| 6,270,788 B1 | * | 8/2001 | Koulik et al. ............. 424/423 |
| 6,387,379 B1 | * | 5/2002 | Goldberg et al. .......... 424/400 |
| 6,828,028 B1 | | 12/2004 | Fukui et al. |

FOREIGN PATENT DOCUMENTS

| | | | |
|---|---|---|---|
| EP | 0947205 A2 | * | 10/1999 |
| EP | 1211268 A1 | * | 6/2002 |
| JP | 06178930 A | * | 6/1994 |
| JP | 9-003207 | | 1/1997 |
| JP | 11-318960 | | 11/1999 |
| WO | WO 93/15775 | * | 8/1993 |
| WO | 01/05855 | | 1/2001 |
| WO | WO 01/07097 A1 | | 2/2001 |

OTHER PUBLICATIONS

Rush S. Butter, et al., "Diamond-Like Carbon for Biomedical Applications (Review)", Journal of Chemical Vapor Deposition, vol. 3, No. 3, Jan. 1995, pp. 182-192.

Williams, III., P.F., et al., "Fabrication and Characterization of Dipalmitoylphosphatidylcholine-Attracting Elastomeric Material for Joint Replacements," Biomaterials, vol. 16, No. 15, Oct. 1995, pp. 1169-1174.

Foy, J. R., et al., "Effect of Phospholipidic Boundary Lubrication in Rigid and Compliant Hemiarthroplasty Models," Proceedings of the Institution of Mechanical Engineers, Part H, vol. 213, No. 1, 1999, pp. 5-18.

* cited by examiner

FIG.1

PHOSPHORYL CHOLINE GROUP
PHOSPHOLIPID
PROTEIN

ARTIFICIAL JOINT MEMBER WITH GRAFTED POLYMER SURFACE

TECHNICAL FIELD

The present invention relates to an artificial joint member made of a polymeric material, and more particularly, to an artificial joint member which is made of a polymeric material and is capable of retaining a satisfactory lubricating state of a sliding part thereof for a long term.

BACKGROUND ART

Considering the actual structure of a human joint in vivo, it is preferable that ciliary substance is arrayed on a sliding surface of an artificial joint member, so that body fluid serving as a lubricating liquid is retainable in the cilia-like substance to provide the sliding surface with a satisfactory lubricating state. It is, however, difficult to artificially create such a state, and it is furthermore difficult to retain such a satisfactory state for a long term. None of the artificial joints has accomplished such a satisfactory state.

Observing the current status of the medical field, combined use of a soft material such as a polymer and a hard material such as a metal is popular for an artificial joint member such as a femoral ball and an acetabular cup. For example, artificial joints each comprised of a metallic femoral ball using stainless steel, cobalt chromium alloy, titanium alloy, or the like and a polymeric acetabular cup using ultra high molecular weight polyethylene (hereinafter, simply called as "UHMW polyethylene") or the like have been implanted in several ten thousand surgeries conducted in a year in Japan. Replacement with such artificial joints is beneficial in relieving patients from pain and releasing them from bedridden state, thus improving their quality of life to a level similar to that of healthy people.

In the aforementioned artificial joint, friction between the metallic member and the polymeric member is generated on the sliding part of the artificial joint frequently owing to physical actions of a person implanted with the artificial joint in his or her daily life. Particularly, wear becomes serious on the side of the polymeric member of the artificial joint. Wear debris of polymer such as UHMW polyethylene is likely to induce osteolysis (bone dissolution), which may cause so-called "loosening" of weakening cohesive strength between the bone and the artificial joint member, and obstruct the function of the artificial joint. The wear debris of UHMW polyethylene generally amounts to 0.1 to 0.2 mm in thickness per year. Generation of wear debris may not be harmful for a certain time after the surgery. However, the loosening becomes intolerable in 5 years or so after the surgery, and replacement with a new artificial joint member is required.

In recent years, proposed is use of so-called (crosslink) polyethylene as means for suppressing wear of the polymer member of the artificial joint. (Crosslinked) polyethylene is a substance in which each molecule of UHMV polyethylene is rendered to a cross-linked state by irradiating a gamma ray or an electron beam onto the UHMW polyethylene. There has been reported that wear debris of such (crosslinked) polyethylene is reduced as low as $\frac{1}{5}$ to $\frac{1}{10}$ in quantity compared with that of ordinary UHMW polyethylene which has not been subjected to irradiation (Biomaterials, Vol. 20 (1999), pp. 1659-1688). However, practice of clinical application of (crosslinked) polyethylene is insufficient, and usability thereof has not been verified.

There has also been proposed combined use of a femoral ball and an acetabular cup both of which are made of a hard material, in place of using a polymer such as the aforementioned UHMW polyethylene which wears easily. For instance, combined use of a femoral ball of cobalt chromium and an acetabular cup of cobalt chromium alloy (Clinicalorthopaedics and Related Research, No. 333 (1996) pp. 96-107), and combined use of a femoral ball of alumina and an acetabular cup of alumina (The Journal of Arthroplasty, Vol. 14, No. 7 (1999) pp. 781-787) are applied to an artificial hip joint clinically. In spite of such a clinical effort, long-term use of the cobalt-chromium femoral ball and the cobalt-chromium-alloy acetabular cup is considered hazardous in that wear debris generated by friction between the cobalt chromium alloys has toxicity to cells in itself.

Further, since the artificial joint comprised of the alumina femoral ball and the alumina acetabular cup may be broken during a surgery operation or in use after the surgery because the alumina is brittle, further improvement is desired to accomplish a successful practical use.

In addition to the above, the aforementioned hard materials are rigid with less elasticity, and do not exhibit cushionability like UHMW polyethylene. Such rigid materials are not desirable because they do not exhibit shock absorbing action to an external force, and a load is directly exerted to the bone.

In view of the aforementioned problems residing in the prior art, it is an object of the present invention to provide an artificial joint member made of a polymeric material which is capable of suppressing generation of wear debris under repeated use in daily life by suppressing friction at a sliding part thereof, and assuring long-term use by providing the artificial joint member with shock absorbability.

DISCLOSURE OF THE INVENTION

An artificial joint member made of a polymeric material according to the present invention has a feature that a sliding surface of the artificial joint member composed of a polymeric substance is made of polymer having phosphoryl choline groups. Preferred examples of the inventive artificial joint member are Examples (1) and (2).

Example (1) in which the phosphoryl choline group is bound to a polymeric substance by way of a (meth)acryloyloxyalkyl group. An example in which polymerizable monomer having the phosphoryl choline group is bound to the polymeric substance by graft bonding is chemically stable, and accordingly desirable.

Example (2) in which a homopolymer or a copolymer of a phosphoryl-choline-containing compound is coated on the polymeric substance. A compound containing (meth)acryloyloxyalkyl phosphoryl choline is recommended as the phosphoryl-choline-containing compound.

A preferred polymeric substance is UHMW polyethylene of one million or more molecular weight. A polymeric substance processed with crosslinking is desirable to secure excellent wear resistance.

The present invention is also directed to an artificial joint incorporated with the inventive artificial joint member made of a polymeric material.

It should be noted that, throughout the present specification and claims, the "polymeric substance" indicates a base part of an artificial joint member, and the "polymeric material" indicates the entirety of the artificial joint member including the "polymeric substance" and the "sliding surface of the artificial joint member composed of polymer having phosphoryl choline groups".

BEST MODE FOR CARRYING OUT THE INVENTION

Under the aforementioned circumstances, the inventors have made research and development, from various viewpoints, about modification of the surface of a polymeric substance used for an artificial joint member under the condition that a polymeric material having a superior shock absorbability to a hard material such as a metal is used for an artificial joint member, so that friction at a sliding part of the artificial joint member is minimized, and wear debris generated by friction is rendered inactive to cells in charge of immune function. As a result of the research and development, the inventors found that forming a compound having a chemical structure similar to that of a cell constituting body tissue on the surface of the polymeric substance is effective, and achieved the present invention. The inventive artificial joint member made of a polymeric material is described in detail in the following.

Figure 1:
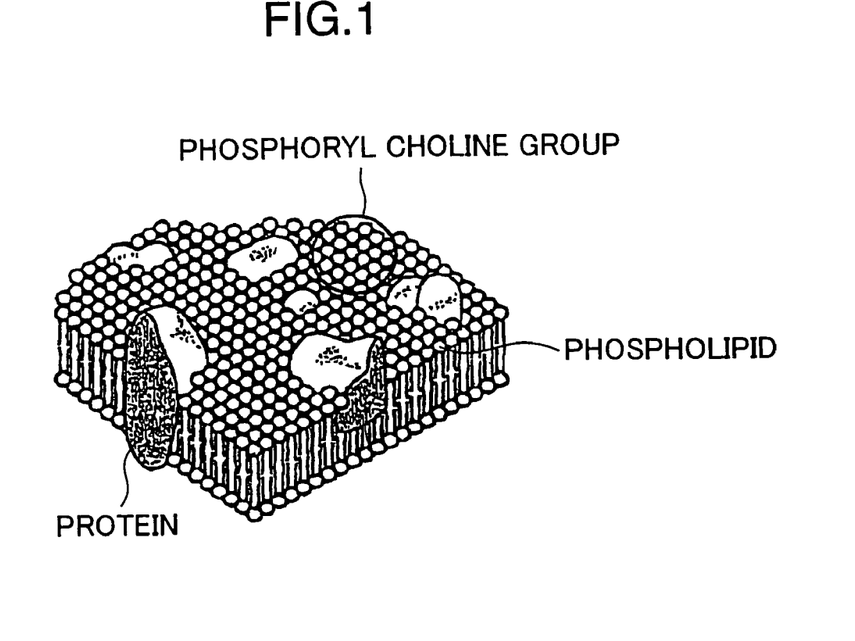
FIG. 1 is a perspective sectional view schematically showing a biomembrane.

As shown in FIG. 1, a biomembrane constituting a surface of a bone such as a joint in vivo is an assembly of phospholipid molecules with its surface substantially covered with phosphoryl choline groups microscopically (Kazuhiko ISHIHARA, Surgery Vol. 61, p. 132 (1999)). In view of this, the inventors found that forming a sliding surface of a femoral ball and/or an acetabular cup of an artificial joint made of a polymeric material, of a polymer having phosphoryl choline groups is advantageous in securing affinity with the lubricating liquid (body fluid) of a patient, which is beneficial in retaining the lubricating liquid and maintaining a desirable lubricating state, and resultantly remarkably reducing friction between the femoral ball and the acetabular cup. Furthermore, since the compound having the phosphoryl choline group has a chemical structure similar to that of a cell constituting body tissue, the compound exhibits desirable biocompatibility without adversely affecting the human body even if wear debris is generated by friction between the femoral ball and the acetabular cup.

The above effects of the present invention are obtained by forming the sliding surface of an artificial joint member made of a polymeric substance, of a polymer having phosphoryl choline groups. The chemical structure of the polymer having phosphoryl choline groups is not specifically limited. However, since a compound in which a phosphoryl choline group is chemically bound to a polymeric substance by way of a (meth)acryloyloxyalkyl group is chemically stable, and is easy to be synthesized by the below-mentioned polymerization method, use of the compound is desirable.

Examples of the methods for yielding a structure in which a phosphoryl choline group is chemically bound to a polymeric substance by way of a (meth)acryloyloxyalkyl group are: a method for directly binding polymerizable monomer to a polymeric substance by graft polymerization; a method for synthesizing a reactive polymer having a phosphoryl choline group, followed by reaction with a polymeric substance; and a method for synthesizing a polymer having a cross-linkable phosphoryl choline group, followed by coating of the polymer onto a polymeric substance, and fixing the coated polymer on the polymeric substance by crosslink reaction. Among these methods, the method for binding polymerizable monomer having a phosphoryl choline group to a polymeric substance by graft polymerization is preferred because the surface of the polymeric substance can be modified without deteriorating the property of the polymeric substance such as rigidity, the bonded part can be chemically stabilized, and the lubricating liquid can be sufficiently retained in the phosphoryl choline groups by forming a multitude of phosphoryl choline groups on the sliding surface of the artificial joint member.

Examples of the polymerizable monomer having a phosphoryl choline group are: 2-methacryloyloxyethyl phosphoryl choline, 2-acryloyloxyethyl phosphoryl choline, 4-methacryloyloxybutyl phosphoryl choline, 6-methacryloyloxyhexyl phosphoryl choline, co-methacryloyloxyethylene phosphoryl choline, and 4-styryloxybutyl phosphoryl choline. Among these, particularly, 2-methacryloyloxyethyl phosphoryl choline (hereinafter, sometimes called as "MPC") represented by the following chemical formula 1 is preferable because the compound consists of a phosphoryl choline group and a unit of polymerizable methacrylic acid and is advantageous in obtaining a polymer of high-molecular weight easily by radical polymerization (Ishihara et al.: Polymer Journal Vol. 22, p. 355 (1990)).

If graft polymerization is conducted with use of the MPC, for example, polymer containing 2-methacryloyloxyethyl phosphoryl choline (hereinafter, sometimes called as "MPC polymer") is bound to a polymeric substance to thereby form a multitude of phosphoryl choline groups on a sliding surface of an artificial joint member. Since the surface of the artificial joint member where the MPC polymer is formed exhibits a conformation analogous to a biomembrane, as shown in FIG. 1, this arrangement is desirable in suppressing friction against a counterpart member of the joint while sufficiently retaining the lubricating liquid and in minimizing reaction with components constituting a living organism or cells.

It should be noted that the present invention embraces such a reaction that graft polymerization is conduced in co-existent with other vinyl compound to thereby yield a copolymer with a phosphoryl-choline-containing compound.

Chemical formula 1

The present invention includes an arrangement in which a homopolymer or a copolymer of a phosphoryl-choline-containing compound is coated on the polymeric substance, as an altered arrangement of the embodiment in which the sliding surface of the artificial joint member made of the polymeric substance is made of the polymer having phosphoryl choline groups.

In such an altered arrangement, similar to the embodiment, it is preferred to use (meth)acryloyloxyalkyl phosphoryl choline, which is an easily-polymerizable compound to yield a polymer, as the phosphoryl-choline-containing compound. Examples of (meth)acryloyloxyalkyl phosphoryl choline are: 2-methacryloyloxyethyl phosphoryl choline, 2-acryloyloxyethyl phosphoryl choline, 4-methacryloyloxybutyl phosphoryl choline, 6-methacryloyloxyhexyl phosphoryl choline, co-methacryloyloxyethylene phosphoryl choline, and 4-styryloxybutyl phosphoryl choline. Among these, it is most preferable to use 2-methacryloyloxyethyl phosphoryl choline showing satisfactory polymerization.

The sliding part made of the polymer having phosphoryl choline groups is formed by preparing an agent in which a homopolymer of a phosphoryl-choline-containing compound, or a copolymer with a vinyl compound, methacrylic acid ester, acrylic acid ester, styrene derivative, or the like, specifically, a copolymer with butyl methacrylate, 2-ethylhexyl methacrylate, butyl acrylate, 2-ethylhexyl acrylate, styrene, or the like is dissolved in a solvent such as ethanol, propanol, or tetrahydrofurane, and by applying the agent on the surface of the polymeric substance by coating, immersion, or a like method.

As another alteration of the embodiment in which the sliding surface of the artificial joint member made of the polymeric substance is made of the polymer having phosphoryl choline groups, it is possible to adopt a blend/molding method comprising the steps of blending the phosphoryl-choline-containing compound with the polymeric substance such as UHMW polyethylene and molding the mixture into a sliding part, or a like method.

It is desirable to use UHMW polyethylene as a polymeric substance constituting a base part of the inventive artificial joint member. The higher the molecular weight, the less wear resulting from sliding movement is likely to occur. In view of this, it is preferable to use UHMW polyethylene of one million or more molecular weight, and more preferably of three millions or more molecular weight.

It is desirable to use the polymeric substance applied with crosslink processing in view of securing excellent wear resistance. A known method for implementing crosslink processing is applicable. Examples of such a known method are irradiation by X-ray, gamma ray, or electron beam, and crosslinking by microwave or ultrasonic wave.

Specific conditions for graft polymerization are not defined in the present invention. There are proposed various methods, in addition to irradiation by an ultraviolet ray in a wavelength band from 300 to 400 nm, as will be described in the below-mentioned examples, polymerization of monomer by generating radicals on a carbon atom by using a compound having a dehydrogenating effect, such as benzoyl peroxide or hydrogen peroxide; and formation of a polymer chain by graft polymerization on the surface of the polymeric substance comprising the steps of adsorbing an aromatic nitro compound or a mercapto compound to the polymeric substance, polymerizing monomer with use of a radical generator in a solvent having a property of inhibiting elusion of the compound, and trapping the generated polymer radicals by the adsorbed aromatic nitro compound or mercapto compound.

In applying the inventive artificial joint member made of a polymeric material to an artificial joint, either one of a femoral ball or an acetabular cup may serve as the inventive artificial joint member while the other one may serve as a member made of a metal such as stainless steel or cobalt chromium alloy, or ceramics such as alumina or zirconia, in addition to the arrangement in which both of a femoral ball and an acetabular cup serve as the inventive artificial joint member.

Further alternatively, a composite arrangement may be adopted in which merely the sliding part of an artificial joint member (a femoral ball and/or an acetabular cup) serves as the inventive artificial joint member, while the remaining part other than the sliding part is composed of a polymeric material other than the polymeric material constituting the inventive artificial joint member, the aforementioned metal, or ceramics.

In view of the foregoing disclosure, in an embodiment of the present invention is an artificial joint member made of a polymeric material comprising:

a sliding surface composed of a homopolymer polymerized from polymerizable monomers each having a phosphoryl choline group and a (meth)acryloyloxyalkyl group wherein the phosphoryl choline group is directly bound to a (meth)acryloyloxyalkyl group;

a part composed of a polyethylene substance, wherein the homopolymer is directly bound to the polyethylene substance at one end of the homopolymer via the (meth)acryloyloxyalkyl group and said homopolymer is produced by graft polymerization of said polymerizable monomers on the surface of said polyethylene substance.

EXAMPLES

In the following, the present invention is illustrated in detail with Examples, which, however, do not limit the present invention. Adequate modification is allowable as far as it does not depart from the object of the present invention described above or below, and every such modification is intended to be embraced in the technical scope of the present invention.

Example I

Wettability

First, wettability of an artificial joint member to a liquid was evaluated as a criterion regarding lubricability of the artificial joint member.

A polymeric layer containing phosphoryl choline groups was formed on a surface of a UHMW polyethylene column member (cross section: 20 mm×20 mm, length: 50 mm) of a molecular weight from three millions to five millions according to the following process.

First, the UHMW polyethylene column member was immersed in an acetone solution containing benzophenone (1.0 g/dL) for 30 seconds, followed by immediate withdrawal from the solution and removal of the solvent at room temperature.

After an aqueous solution containing 0.5 mol/L of MPC (2-methacryloyloxyethyl phosphoryl choline) was de-aired sufficiently, the column member with sufficient adsorption of benzophenone was immersed in the aqueous solution. Subsequently, the column member was subjected to irradiation by an ultraviolet ray in a wavelength band from 300 to 400 nm at a liquid temperature of 60° C. for 30 minutes. Thereafter, the sample (column member) was washed with purified water sufficiently, thereby yielding a test sample with formation of MPC polymer on the surface thereof.

The surface of the test sample with formation of the MPC polymer was examined with an X-ray photoelectron spectrometer. In the test, detection of a signal indicative of a nitrogen atom of 399 eV and a signal indicative of a phosphorous atom of 133 eV was judged as the presence of a phosphoryl choline group in the MPC on the surface of the test sample made of a polymeric material.

A UHMW polyethylene column member (processed member) with formation of the MPC polymer, and a UHMW polyethylene column member (unprocessed member) without formation of the MPC polymer were used as test samples, and wettability of the respective test samples was evaluated. Wettability was examined by measuring a contact angle of a liquid droplet relative to the surface of the test sample by dropping one droplet (of about 30 mm³ in volume) of the liquid shown in Table 1 onto the surface of the test sample. The results of the measurement are shown in Table 1.

TABLE 1

| Kind of liquid | Contact angle (°) | |
| --- | --- | --- |
| | MPC polymer not-formed (unprocessed) | MPC polymer formed (processed) |
| purified water | 90 | 10 |
| blood | 80 | 30 |
| body-fluid-like substance | 75 | 10 |

As is obvious from Table 1, the processed column member with formation of the MPC polymer showed a remarkably small contact angle in every case of dropping the liquids, compared with the unprocessed column member without formation of the MPC polymer, thus proving that the processed member has a satisfactory wettability.

Example II

Friction Coefficient

Next, the lubricability of the artificial joint member was evaluated based on a friction coefficient.

Each of the test samples obtained in a similar manner as Example I was pressed with an end of a metallic rod of 5 mm in diameter having the composition shown in Table 2 with purified water interposing between the rod and the test sample as a lubricating liquid, a load corresponding to a surface pressure of 1 N/cm² was exerted to the contact surface of the column member (test sample) and the metallic rod at a right angle to the contact surface, and a friction coefficient was calculated by sliding the metallic rod relative to the surface of the column member (test sample) at a velocity of 100 mm/min. The results of the test are shown in Table 2.

TABLE 2

| Kind of metal | friction coefficient | |
| --- | --- | --- |
| | MPC polymer not-formed (unprocessed) | MPC polymer formed (processed) |
| brass (copper:zinc = 6:4) | 0.689 | 0.242 |
| stainless steel | 0.855 | 0.221 |

It is clear from Table 2 that the processed member with formation of the MPC polymer has a smaller friction coefficient, and thus provides remarkably improved lubricability. It is conceived that such a superior lubricability is achieved because hydrophilicity is enhanced owing to the formation of the MPC polymeric layer corresponding to several layers of molecules on the surface of the artificial joint member, and the formation of the layer having a free-water content as high as about 90% in maximum on the surface of the artificial joint member.

Example III

Friction Test by Pivotal Rotation (1)

A test regarding friction by pivotal rotation was conducted with respect to an artificial joint model in which a UHMW polyethylene cup was used as an acetabular cup, and a stainless-steel ball was used as a femoral ball.

Figure 2:
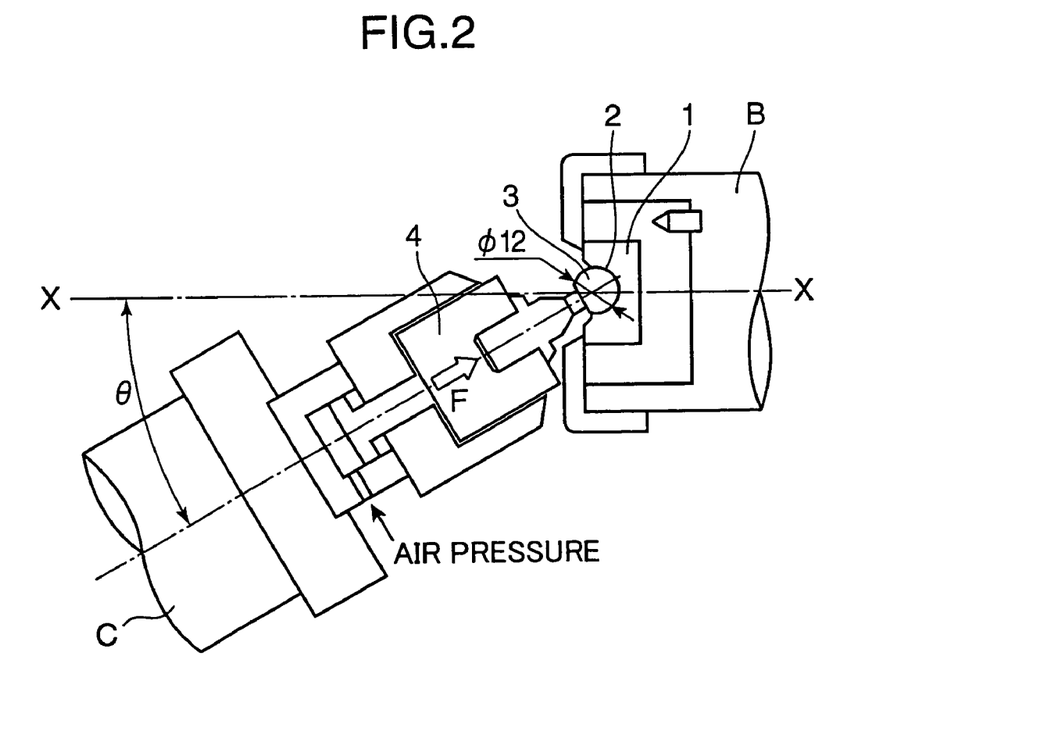
FIG. 2 is a schematic side view showing an apparatus for measuring friction by pivotal rotation used in Example I.

FIG. 2 is a diagram showing an apparatus for measuring friction by pivotal rotation. The apparatus is constructed such that: a UHMW polyethylene cup 1 (molecular weight: three millions to five millions) formed with a hemispherical recess 2 having a diameter of 12.10 mm is mounted on a main shaft B which is freely rotated about a primary axis of rotation X-X; a spherical body 3 of a stainless steel (SUS316) having a diameter of 12.00 mm is mounted on a jig; and the spherical body 3 is pivotally and tiltingly rotated about an axis of its support shaft relative to the primary axis of rotation X-X by an arbitrary angle θ in a state that the spherical body 3 is pressed against the recess 2 (inner wall) of the cup 1 by the force F owing to supply of an air pressure. The spherical body 3 is driven by a motor (not shown) whose rotating number per unit time is adjustable. An arm is mounted on the main shaft B to measure a friction torque under the condition that the main shaft B is forcibly about to be rotated by a frictional force accompanied by pivotal rotation of the spherical body 3. The surface roughness of the spherical body 3 is set at Ra 0.02 μm. Two kinds of UHMW polyethylene cups 1 were used: one (processed cup) with the recess 2 being formed with MPC polymer as mentioned above, and the other (unprocessed cup) with the recess 2 not being formed with MPC polymer. The following experiments (i) through (iii) were conducted with use of the aforementioned apparatus.

Experiment (i)

First, friction torque and variation in friction torque (variation per rotation) were examined with respect to the processed cup and the unprocessed cup by varying a pressing load, as shown in Table 3. The results of the experiment are shown in Table 3.

TABLE 3

| Ex. No. | Load F (N) | Formation of MPC polymer | Torque (N · cm) | Torque variation |
| --- | --- | --- | --- | --- |
| 1 | 39.2(4 kgf) | no | 1.43 | small |
| | | yes | 0.19 | negligibly small |
| 2 | 58.8(6 kgf) | no | 3.00 | large |
| | | yes | 0.28 | negligibly small |
| 3 | 78.4(8 kgf) | no | 5.14 | large |
| | | yes | 0.52 | negligibly small |
| 4 | 98(10 kgf) | no | 8.43 | large |
| | | yes | 0.85 | negligibly small |

As is obvious from Table 3, there is a tendency that the larger the load, the larger the friction torque irrespective of formation/non-formation of the MPC polymer. However, the processed cup with formation of the MPC polymer has a friction torque of an extremely small absolute value with a negligibly small variation in friction torque, thus proving that formation of the MPC polymer contributes to reduction of friction.

Experiment (ii)

Variation in friction torque was observed with respect to formation and non-formation of the MPC polymer under the condition that the apparatus was operated without supply of purified water as a lubricating liquid at an initial stage of operation, followed by supply of purified water as a lubricating liquid between the spherical body 3 (serving as a femoral ball) and the cup 1 (serving as an acetabular cup) upon lapse of a certain time from the start-up of the apparatus. The pressing load was set at 98N. The results of the experiment are shown in FIG. 3.

Figure 3:
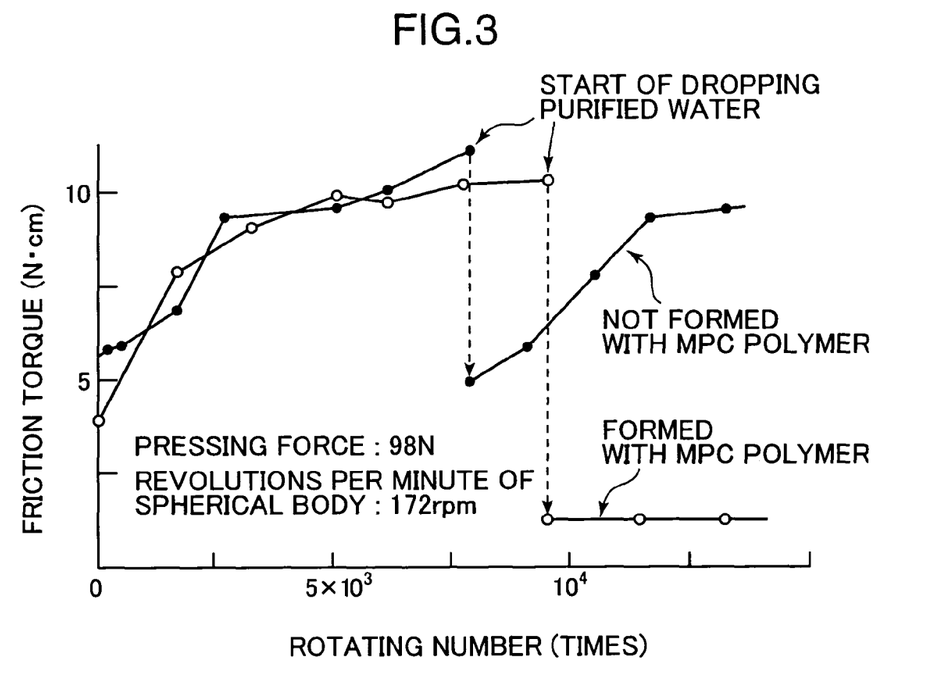
FIG. 3 is a graph showing a variation in friction torque at the time of dropping purified water based on formation or non-formation of MPC polymer.

As is obvious from FIG. 3, observing the unprocessed UHMW polyethylene cup without formation of the MPC polymer, as the rotating number (sliding distance) increased, friction torque increased. After the supply of purified water, the friction torque temporarily decreased. However, eventually, the friction torque sharply increased. On the other hand, observing the processed UHMW polyethylene cup with formation of the MPC polymer, friction torque gradually increased from the sliding start time. However, as purified water was supplied, the friction torque sharply decreased with the result that the friction torque was retained at a low level. It is conceived that such a phenomenon results from reduction of friction because a satisfactory lubricating state is secured for a long time by keeping the purified water in the MPC polymer.

Experiment (iii)

Next, variation in friction torque was examined with respect to formation and non-formation of MPC polymer under the condition that the sliding distance is increased by increasing the rotating number.

In the experiment, sliding movement was carried out while supplying purified water as a lubricating liquid at a feeding rate of 5.6 mL/min. between the spherical body 3 (serving as a femoral ball) and the cup 1 (serving as an acetabular cup). The pressing load was set at 98N. The results of the experiment are shown in FIG. 4 as a relation between the number of rotations (sliding movements) and a friction torque with respect to formation and non-formation of MPC polymer.

Figure 4:
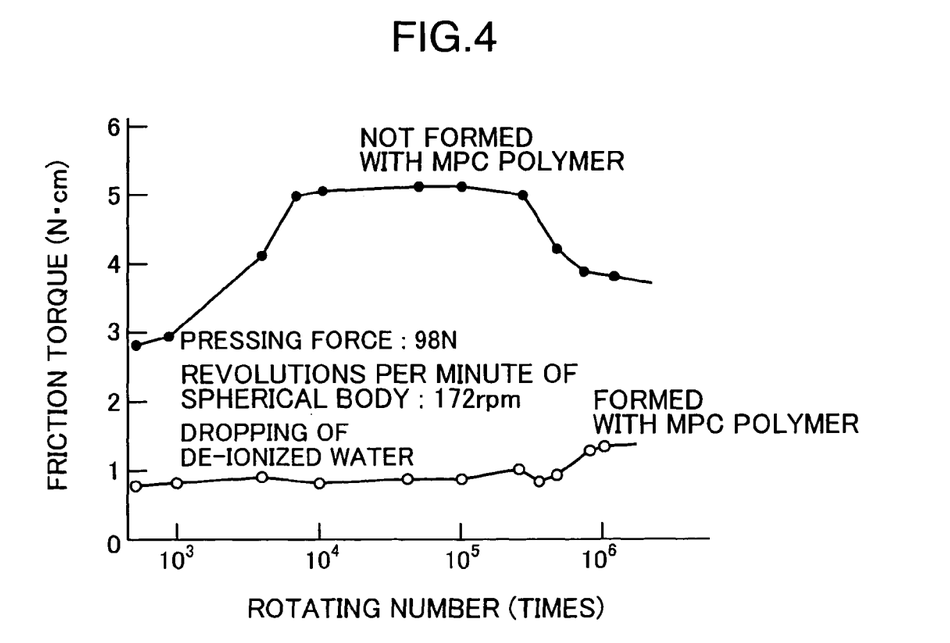
FIG. 4 is a graph showing a relation between the number of rotations of the apparatus and a friction torque based on formation or non-formation of MPC polymer.

As is obvious from FIG. 4, the UHMW polyethylene cup with formation of MPC polymer retained a low friction torque irrespective of the sliding number. On the other hand, the unprocessed UHMW polyethylene cup without formation of MPC polymer showed increase in friction torque from the sliding start time, as the number of rotations increased, and showed a tendency that the friction torque temporarily decreased after retaining a high friction torque state for a while. It is conceived that such a temporary reduction in friction torque seen in the unprocessed cup without formation of MPC polymer indicates that the cup reached a so-called constant wear zone, which is generally observed in a wear phenomenon, namely, the sliding surface of the cup was brought to a wear tolerable state. In actual use, however, wear debris is generated in large quantity until the cup reaches such a zone, which is not desirable because the loosening may occur before the cup reaches the zone. In FIG. 4, friction torque with respect to the processed cup with formation of MPC polymer after one million times of rotations was less as about ¼ as friction torque with respect to the unprocessed cup without formation of MPC polymer, thus proving that friction is remarkably suppressed with respect to the processed cup after long-term use.

Example IV

Wear Test by Pivotal Rotation (2)

A test was run to confirm that crosslink processing of a polymeric substance forming an artificial joint member is effective in improving wear resistance of the artificial joint member.

A test concerning wear by pivotal rotation was conducted with respect to artificial joint models each constructed by a pair of a crosslink-processed UHMW polyethylene cup as an acetabular cup, and a commercially available cobalt chromium alloy ball (diameter: 22 mm) as a femoral ball, and by a pair of a crosslink-unprocessed UHMW polyethylene cup as an acetabular cup, and a commercially available cobalt chromium alloy ball (diameter: 22 mm) as a femoral ball. Both of the crosslink-processed cup and the crosslink-unprocessed cup have been formed with MPC polymer according to the aforementioned process. The crosslink processing was conducted by irradiating a gamma ray of 5 Mrad in intensity onto the UHMW polyethylene cup for 320 minutes.

Figure 5:
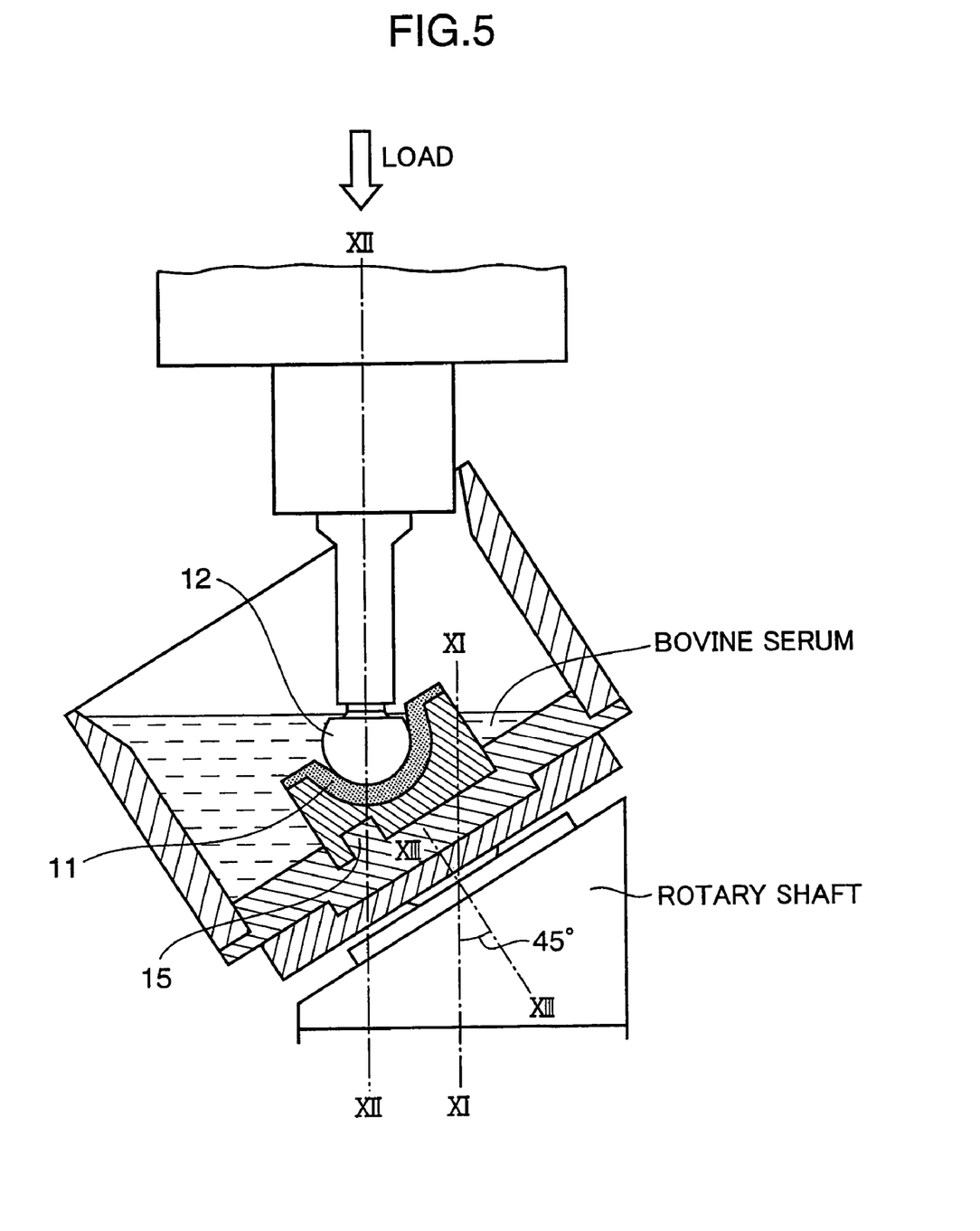
FIG. 5 is a schematic side view showing an apparatus for measuring friction by pivotal rotation used in Example IV.

The wear test was conducted by a wear measuring apparatus manufactured by Metering Technology Corporation (MTC). FIG. 5 is a schematic side view of the apparatus. In the test, as shown in FIG. 5, a base plate was disposed tiltingly relative to a lower primary axis of rotation XI-XI by 45°, and a UHMW polyethylene cup 11 was fixed to the base plate. The quantity of wear debris of the cup 11 was measured by pivotally rotating a rotary shaft about a lower primary axis of rotation XIII-XIII while pressing a spherical body (acetabular ball) 12 against a recess of the cup 11. The spherical body 12 is pivotally mounted about an upper primary axis of rotation XII-XII. The pressing load was set at 2744N (280 kgf), the cycle of rotations was 1 Hz, and a variation in load per cycle of rotations was in conformity with a walking curve of Poul.

In this experiment, the wear test was conducted under the condition that the cup 11 and the spherical body 12 were immersed in bovine serum (25 mass %) of 37° C. to evaluate wear resistance of the cup 11 in a state analogous to an in-vivo state. The bovine serum was replaced every 500,000 times of rotations.

In this way, the wear test was conducted with respect to the crosslink-processed UHMW polyethylene cup 11 with formation of MPC polymer and the crosslink-unprocessed UHMW polyethylene cup 11 with formation of MPC polymer. The masses of the respective cups 11 were measured every 500,000 times of rotations. The quantity of wear debris of each cup 11 was calculated based on a difference in the mass of the cup 11 between before and after the wear test. The results of calculation are shown in FIG. 6 as a relation between the number of cycle of rotations and the quantity of wear debris of the cup.

Figure 6:
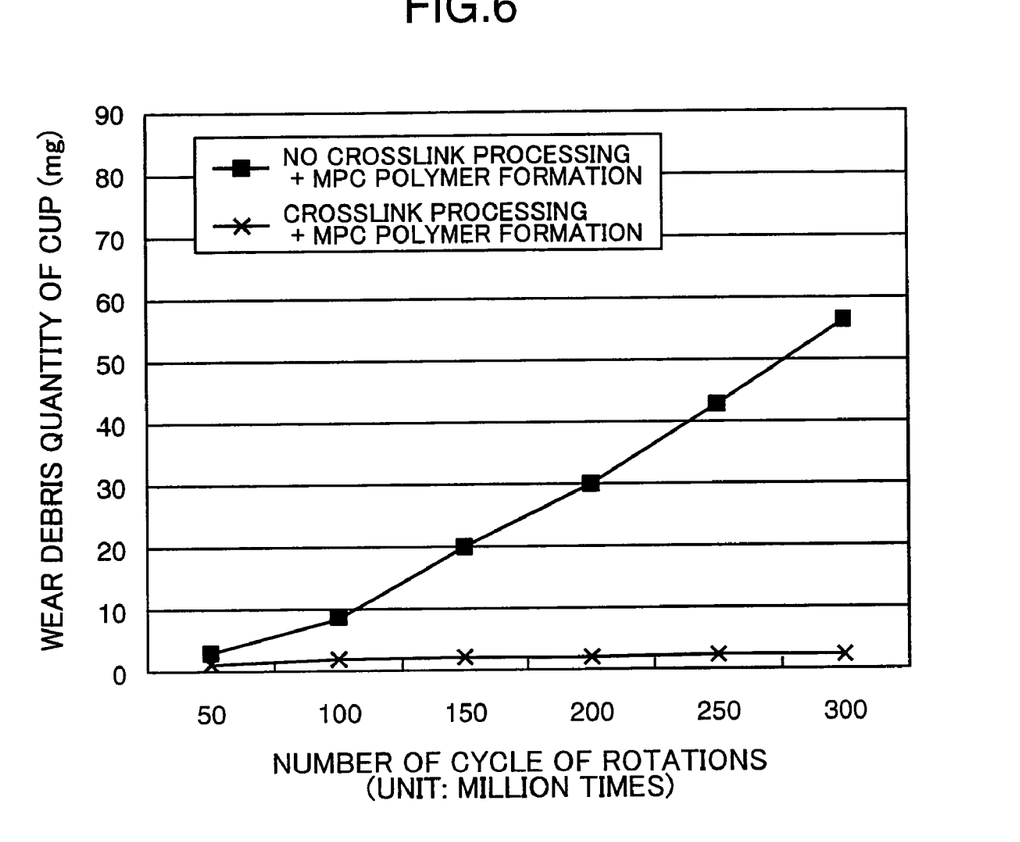
FIG. 6 is a graph showing a relation between the number of cycle of rotations of the apparatus and the quantity of wear debris of UHMW polyethylene cup based on crosslink processing or non-processing.

As is obvious from FIG. 6, use of the crosslink-processed UHMW polyethylene cup is effective in suppressing the quantity of wear debris of the cup to a significantly low level even under a condition of such an extremely long sliding distance corresponding to a cycle of rotations of 3 million times of rotations. In other words, use of the crosslink-processed polymeric material for a base part of an artificial joint member is advantageous in further reinforcing wear resistance established by formation of MPC polymer.

EXPLOITATION IN INDUSTRY

The present invention has been constructed as mentioned above. According to the present invention, a satisfactory lubricating state is secured for a long term. As a result, provided is an artificial joint member having remarkably less wear and excellent shock absorbability. By using an artificial joint incorporated with the inventive artificial joint member, a patient can live his or her daily life with a similar quality of life as a healthy person for a long term.

The invention claimed is:

1. An artificial joint member made of a polymeric material comprising:
    a sliding surface composed of a homopolymer polymerized from polymerizable monomers each having a phosphoryl choline group and a (meth)acryloyloxyalkyl group wherein the phosphoryl choline group is directly bound to a (meth)acryloyloxyalkyl group;
    a part composed of a polyethylene substance,
    wherein the homopolymer is directly bound to the polyethylene substance at one end of the homopolymer via the (meth)acryloyloxyalkyl group and said homopolymer is produced by graft polymerization of said polymerizable monomers on the surface of said polyethylene substance.

2. The artificial joint member of claim 1, wherein the polymerizable monomer is (meth)acryloyloxyalkyl phosphoryl choline.

3. The artificial joint member of claim 1, wherein the polyethylene substance is ultra high molecular weight polyethylene of one million or more molecular weight.

4. The artificial joint member of claim 1, wherein the polyethylene substance is a crosslink-processed polyethylene.

5. An artificial joint incorporated with the artificial joint member of claim 1.

6. An artificial joint incorporated with the artificial joint member of claim 2.

7. An artificial joint incorporated with the artificial joint member of claim 3.

8. An artificial joint incorporated with the artificial joint member of claim 4.

* * * * *